United States Patent
Loffredo et al.

(10) Patent No.: US 7,278,579 B2
(45) Date of Patent: Oct. 9, 2007

(54) PATIENT INFORMATION MANAGEMENT SYSTEM

(75) Inventors: Cathy A. Loffredo, Tucson, AZ (US);
Michael Treat VanSickler, Columbia, MD (US); Christopher Brian Godschall, Ellicott City, MD (US);
Victor Macleau Ebeneza Kaitell, Villa Rica, GA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 11/274,690

(22) Filed: Nov. 14, 2005

(65) Prior Publication Data

US 2006/0180659 A1 Aug. 17, 2006

Related U.S. Application Data

(60) Provisional application No. 60/627,644, filed on Nov. 12, 2004.

(51) Int. Cl.
*G06K 7/10* (2006.01)

(52) U.S. Cl. ............ 235/462.46; 235/472.02; 235/375

(58) Field of Classification Search .......... 235/462.46, 235/472.02, 375; 705/3
See application file for complete search history.

(56) References Cited

U.S. PATENT DOCUMENTS

| | | | |
|---|---|---|---|
| 2002/0026331 A1* | 2/2002 | Case | 705/3 |
| 2003/0114176 A1* | 6/2003 | Phillipps | 455/500 |
| 2004/0203662 A1* | 10/2004 | Boldon | 455/414.1 |
| 2005/0033603 A1* | 2/2005 | Suzuki et al. | 705/2 |
| 2005/0144044 A1* | 6/2005 | Godschall et al. | 705/3 |

* cited by examiner

*Primary Examiner*—Michael G. Lee
*Assistant Examiner*—Kristy A. Haupt
(74) *Attorney, Agent, or Firm*—Alexander J. Burke

(57) ABSTRACT

A system and method are disclosed for an improved patient information management system in a medical setting. The present invention relates to a remote patient information system and method comprising workstations, handheld computers, and wireless portable printers or portable-computing and labeling systems that facilitate the fulfillment of orders for patient specimen collection performed manually in hospital environments. A handheld device receives and uses printer identifier information in order to establish a wireless temporary local area network thereby causing the printer to be dedicated to printing information solely from the handheld device for a predetermined number of patients. Information such as labels or messages are printed in order to facilitate tracking of patient information.

25 Claims, 14 Drawing Sheets

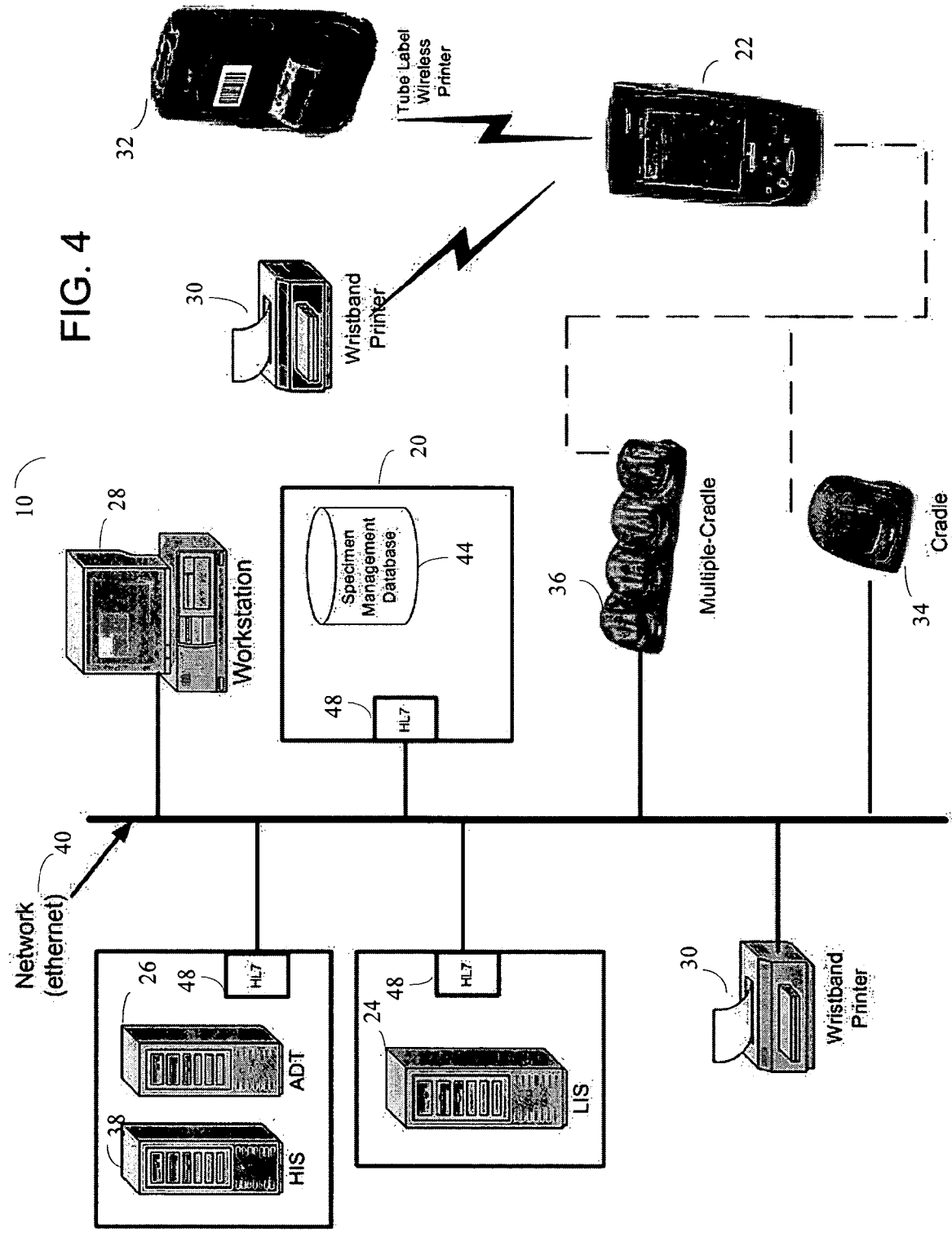

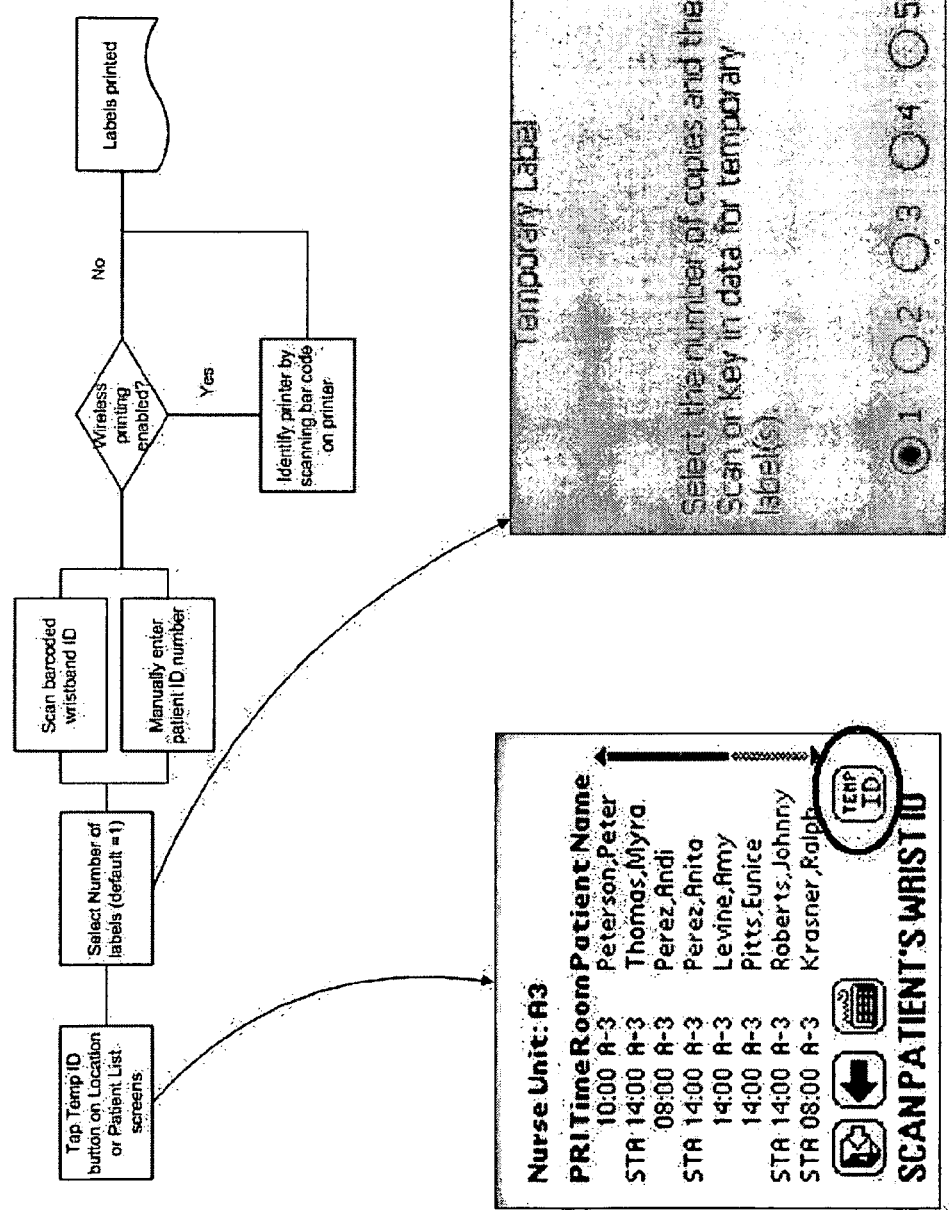
Figure 5B: Feature: Option to select and print multiple Temp ID labels for a Patient

FIG. 6

Old Orders on the Web Page

Old orders are displayed in inverse color.

FIG. 7
Patient List - Past Due Orders
Patients with Past Due Orders are Highlighted in Blue Text
When a patient with past due orders is identified for specimen collection, the system displays a warning:
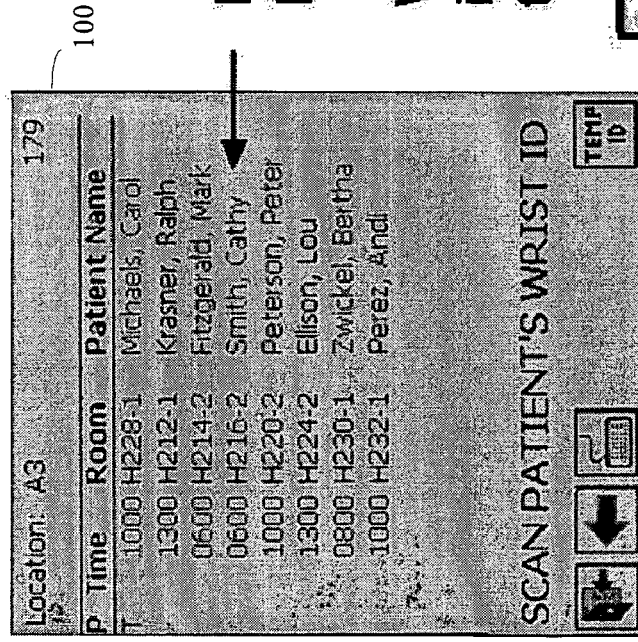
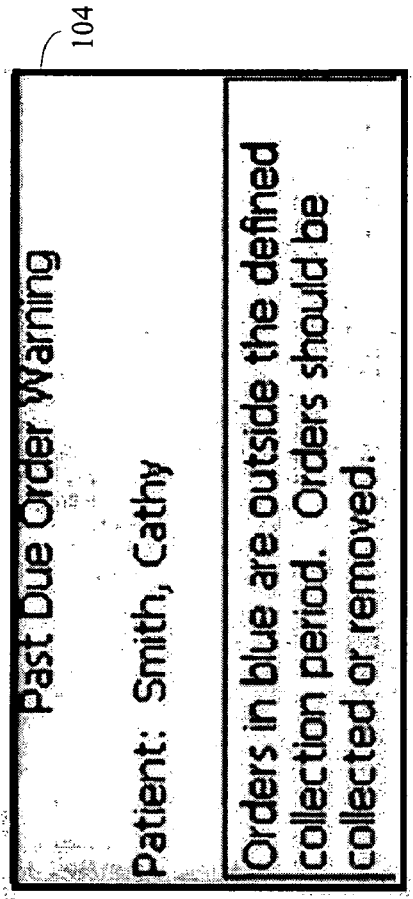

FIG. 8

Timed Test Alert

The Flashing Timed Test icon indicates there are patient(s) with Timed Test(s) ordered.

Tap the icon to view a message showing the location of the patient(s).
If logged in, the message also includes the patient name(s).

FIG. 11

| Msg Type | Order Cnt | Add Patient to DB | ReAdmit | Update All on ReAdmit | Name | DOB/ Gender | Location | Use Previous Location | Account | Extended Patient Data | Extend Account | Discharge Account | Patient | Patient Immed |
|---|---|---|---|---|---|---|---|---|---|---|---|---|---|---|
| A01 | | Yes | Yes | Yes | Yes | Yes | Yes | No | Yes | Yes | Yes | No | No | No |
| A02 | | Yes | Yes | No | No | Yes | Yes | No | No | No | No | No | No | No |
| A03 | | Yes | No | No | Yes | Yes | No | No | Yes | Yes | Yes | Yes | No | No |
| A04 | | Yes | Yes | No | Yes | Yes | Yes | No | Yes | Yes | No | No | No | No |
| A06 | | No | Yes | No | Yes | Yes | Yes | No | No | No | No | No | No | No |
| A07 | | Yes | No | No | No | No | No | No | No | No | No | No | No | No |
| A08 | | Yes | No | No | Yes | Yes | Yes | No | Yes | Yes | No | No | No | No |
| A11 | | No | No | No | No | No | No | No | No | No | No | No | Yes | Yes |
| A12 | | Yes | Yes | Yes | Yes | Yes | Yes | No | No | No | No | No | No | No |
| A13 | | Yes | Yes | No | No | No | Yes | No | Yes | No | Yes | No | No | No |
| ORM | CA | Yes | No | No | No | No | No | No | Yes | No | No | No | No | No |
| ORM | NW | Yes | Yes | Yes | Yes | Yes | Yes | No | Yes | No | Yes | No | No | No |
| ORM | RC | Yes | Yes | Yes | Yes | Yes | Yes | No | Yes | No | Yes | No | No | No |

FIG. 12

PATIENT INFORMATION MANAGEMENT SYSTEM

CROSS REFERENCE TO RELATED APPLICATIONS

This applications claims priority to, and the benefit of, U.S. Provisional Patent Application Ser. No. 60/627,644 filed on Nov. 12, 2004 which is hereby incorporated by reference in its entirety.

BACKGROUND OF THE INVENTION

Field of the Invention

The present invention generally relates to remote networked patient information systems, and methods for using and operating the same. In particular, the present invention relates to a remote patient information system having functionality to monitor, facilitate, and audit medical services. This functionality can be achieved with a reader for reading bar-coded products such as specimen collection containers, and a portable printer for printing labels that include patient information and barcodes for specimen collection containers at the site of patient sample collection. Additionally, the present invention can also apply to patient information management systems for reading and labeling containers or vessels containing therapeutics such as infusible medication.

More specifically, the present invention relates to a remote patient information management system comprising workstations, handheld computers, and portable printers or portable-computing and labeling systems that facilitate the fulfillment of orders for patient specimen collection performed manually in hospital environments by providing advanced label printing capability, by providing capability to print wirelessly from handheld computers to portable printing devices, by highlighting older orders on the handheld device that need processing, by generating an alert on the handheld device to indicate that an order requiring a timed test is overdue, by generating a warning on the handheld device to ensure the proper processing of patient information when the user is working with information for multiple patients, and by providing the ability to completely process and manage patient information at any patient information workstation.

Patient tracking, data management, and the order of medication and sample collection in a hospital environment are typically performed by a network that includes an Admission, Discharge, and Transfer server (ADT), a Laboratory Information System (LIS) and a Hospital Information System (HIS). The ADT, LIS, and HIS systems fall under the general category of Health Care Information Systems.

In providing patient care, health care workers typically utilize one or more software applications accessible through a health care information system. Access to these systems has typically required fixed terminals, such as nurse workstations, to be used at locations distant from the patient's location. To provide more convenient and efficient access to a health care information system, more portable modules such as handheld computers have recently been introduced into health care and hospital settings and are hereinafter generally referred to as "handhelds". Handhelds can be connected to a server directly through a LAN, modem, or wireless connection. Optionally, the handhelds can be connected to a server through a PC using a serial or parallel connection. In order to use the handheld, the information available on the handheld is synchronized with the health care information system by connecting the handheld to a data import/export device connected to the system, or via a cable connected to the system, to allow the exchange of data between the system and the handheld.

Current health care systems that utilize handheld devices provide basic functionality to monitor patient tasks. A need therefore exists to be able to program the handhelds with additional functionality to allow a user to fully process patient information and to provide alerts or warnings to guide users in performing tasks.

The handhelds can be coupled with printers with wireless capability in order to allow patient processing at the patient's location. The printers can be dedicated for use with a particular handheld through a variety of methods.

There are two common protocols for enabling wireless printing: Bluetooth and WiFi (IEEE 802.11b protocol). In the hospital setting, the Bluetooth protocol is a more advantageous system because WiFi requires a costly and elaborate infrastructure to be put in place in the hospital in order to operate.

Bluetooth is a software and hardware system embedded in devices to enable them to identify themselves to each other, determine whether or not information should be transferred to one another via radio frequency, and to transfer information necessary to effect data transfer or the activation of a process such as printing. The hardware required are a radio transmitter and a receiver operating at defined frequency and scanning rates according to the Bluetooth standard. The software, referred to as a "stack" on a device, is written to conform to the Bluetooth protocol. The software directs the device to discover other devices that are transmitting an identifying signal known as the MAC address of the device. The MAC address of a device that is detected is programmed into the detecting device. The two devices then engage in a process known as a "handshake" by which they establish a radio frequency link similar to establishment of a temporary local area network (called a "piconet"). When the handshake is complete, the devices exchange information that allows them to complete the objective. Once the objective is complete, the piconet is dissolved.

The ability to print with a wireless connection to a printer using Bluetooth technology is significant in hospital settings. Connecting and disconnecting a cable to a handheld device or printer is time consuming and can lead to mechanical failure of the cable via bending of pin connectors or shorting due to frayed wiring within the cable. Cabling can cause broken hospital equipment, supplies or patient specimens when a user attempts to carry the handheld device beyond the length of the cable or when emergency situations arise that require sudden movement of hospital personnel.

Notwithstanding its advantages, use of standard Bluetooth technology in a hospital setting can be problematic. For example, communication between a handheld and a printer to enable printing is slower than using a cabled mode of operation because the Bluetooth discovery process can take up to several seconds to identify a suitable printer. In addition, if the handheld device detects multiple printers enabled for Bluetooth communication in close proximity during the discovery phase, as will be common in the hospital setting, the Bluetooth protocol will direct the user to choose a printer from the detected list by MAC address or a familiar name. This could cause delays and potential misrouting of printed labels if the user is not familiar with a printer's ID or is working in low-light settings that exist in certain hospital locations.

The above-described inefficiencies could be time consuming and potentially dangerous if patient samples get mixed up or lost as a result. In addition, discomfort to the patient will result if additional sample collection is required. A need therefore exists for a way to dedicate a particular wireless printer to a handheld device in different hospital settings to ensure quick and easy printing of specimen collection or medical form labels at the patient's location.

SUMMARY OF THE INVENTION

The proposed invention allows a hospital or laboratory technician such as a phlebotomist, doctor, or nurse to improve specimen collection order fulfillment and to reduce medical errors when collecting patient specimens.

An object of the present invention is to provide a means to fully process patient information and provide alerts or warnings to users of the system.

Another object of the present invention is to provide a means of dedicating a printer with wireless capability to a handheld device by scanning an identifying barcode on the printer after disabling the discovery function of a wireless communication protocol.

In accordance with an aspect of the invention, functionality is created in the handheld to: (i) allow the user to generate one or more temporary identification labels, (ii) receive information from the health care information system, identifying old orders, display patient information for old orders in a text format distinguishable from the text format used for current or new orders, and display a warning message informing the user that the order is overdue, (iii) display a flashing icon that indicates there is a patient with timed tests ordered, and (iv) display a warning indicating that a new patient has been identified when a user views patient information on the handheld and then scans the barcode of a different patient.

In accordance with another aspect of the invention, a message is sent by the LIS to the patient information system to indicate that a specimen has been received in the lab and the status of the corresponding system entries are then changed to a "Received by lab" message. This status removes any pending orders corresponding to the received specimens from the Pending Specimen List on the web page of the patient information management system. More specifically, this aspect of the patient information management system includes functionality to: (i) close orders (i.e. remove them from the patient information system) for non-covered locations that might be inserted into the system, (ii) close orders collected outside the patient information system in covered locations, and (iii) close orders as soon as the order is identified as being received in the lab or the collecting handheld is docked, whichever comes first.

In accordance with another aspect of the invention, the patient information management system includes functionality to control what ADT data (e.g. patient name, patient date of birth, etc.) is allowed to update the corresponding fields of the patient information management system.

In accordance with another aspect of the invention, the discovery function of a standard wireless protocol is disabled and functionality is created in order to allow the handheld device to link to a printer by receiving printer identifier information through means such as, for example, manually scanning a barcode identifying that printer or receiving information from an RFID.

In an embodiment of the present invention, a system administrator sets one of three print modes for each location (e.g. nursing unit) in the health care facility as the default printing mode to specify whether a cabled mode or one of two wireless modes is used. If the Per Patient wireless mode is chosen, a particular printer with wireless capability is dedicated to a handheld device by scanning the printer ID barcode resident on the printer after or in connection with a patient specific process step indicating to the handheld that an upcoming scan of a printer barcode will assign that printer to the specific patient. If the Linked wireless mode is chosen, a particular printer with wireless capability is dedicated to a handheld device by scanning the printer ID barcode resident on the printer and the chosen printer then can be used for multiple patients until the user chooses a new printer by scanning another printer identification barcode. The system allows the user to override the default printer mode through a menu option on the handheld device if necessary.

As shown in FIGS. 1 through 4, the system 10 of the present invention may be combined in one of several configurations with the components of existing Health Care Information systems (ADT 26, LIS 24, HIS 38, HIS/LIS Data Interface 48, Wristband Printer 30, etc.). The basic components of the present invention are a patient information system workstation 28, a server 20, a portable medical handheld device 22, a miniature identification barcode reader 22, and a printer with wireless capability 32. The server 20 contains a Specimen Management Database 44 to track specimen collections for all patients.

The identification code reader could be a barcode scanner, imager, radio frequency identification ("RFID"), infrared identification reader or similar technology. An example of such a portable computing device is the Symbol Technologies PPT 8800 Series Pocket PC. The handheld device preferably comprises features that include barcode scanning and real-time wireless communication options.

The subcomponents of the medical handheld device may be a battery, display, keyboard, cradle, wireless communications circuitry, memory, housing, and central processing unit (CPU). The medical handheld device can be any portable diagnostic monitor such as a portable data assistant (PDA), notebook computer, tablet PC, or other device. An identification code reader can be integrated into the medical handheld device or attached to the medical handheld device via an accessory device. The reader could potentially be detachable from the handheld device. A cradle 34 is a docking station used to provide an interface with a host terminal. The cradle 34 can be customized to receive and secure the handheld 22. A multiple-cradle unit 36 can be used to dock multiple handheld devices at one time. A detector element may be included to detect when the handheld 22 is placed in the cradle. Data can be received from a server 20 and selectively downloaded when the handheld is placed in the cradle 34. Likewise, data from the handheld 22 can be sent by the handheld or retrieved by the server 20 when the handheld is placed in the cradle 34. An actuator on the handheld may be employed for initiating the transfer of data from the handheld to the server 20 when the detector indicates that the handheld 22 has been placed in the cradle 34.

Along with carrying the portable medical handheld device, which may have a barcode scanner attached or integrated inside, a nurse or phlebotomist may also carry a portable wireless printing device for printing labels that include patient information and barcodes at the site of patient sample collection. An example of such a portable wireless printing device is the network addressable Zebra Model QL-220 direct thermal mobile printer. The printer 32 comprises features such as a unique network address and real-time wireless communication options.

The specimen collection tube labels 52 that are printed include patient-specific information and the unique collection tube barcode originally provided by the LIS 24 and uploaded to the handheld 22 with then patient data, order and specimen container information. In a preferred embodiment of the present invention, the specimen collection container barcode is first scanned to ensure the correct container is used, and then a specimen label is printed that includes the barcode sent from the LIS 24.

BRIEF DESCRIPTION OF THE DRAWINGS

These and other aspects, advantages and novel features of the present invention will be readily comprehended from the following detailed description when read in conjunction with the accompanying drawings:

FIGS. 1, 2, 3 and 4 each illustrate a client handheld and printers configured in accordance with the present invention in use with different configurations of a health care information system;

FIGS. 5A and 5B depict logic diagrams and screen displays corresponding to the temporary identification function in accordance with an embodiment of the present invention;

FIGS. 6, 7, and 8 depict exemplary alert and warning display screens in accordance with an embodiment of the present invention;

FIGS. 11 and 12 depict screen displays of the web page interface for configuring which ADT parameters will be sent to the patient information management system in accordance with an embodiment of the present invention.

DETAILED DESCRIPTION OF THE PREFERRED EMBODIMENTS

Figure 1:
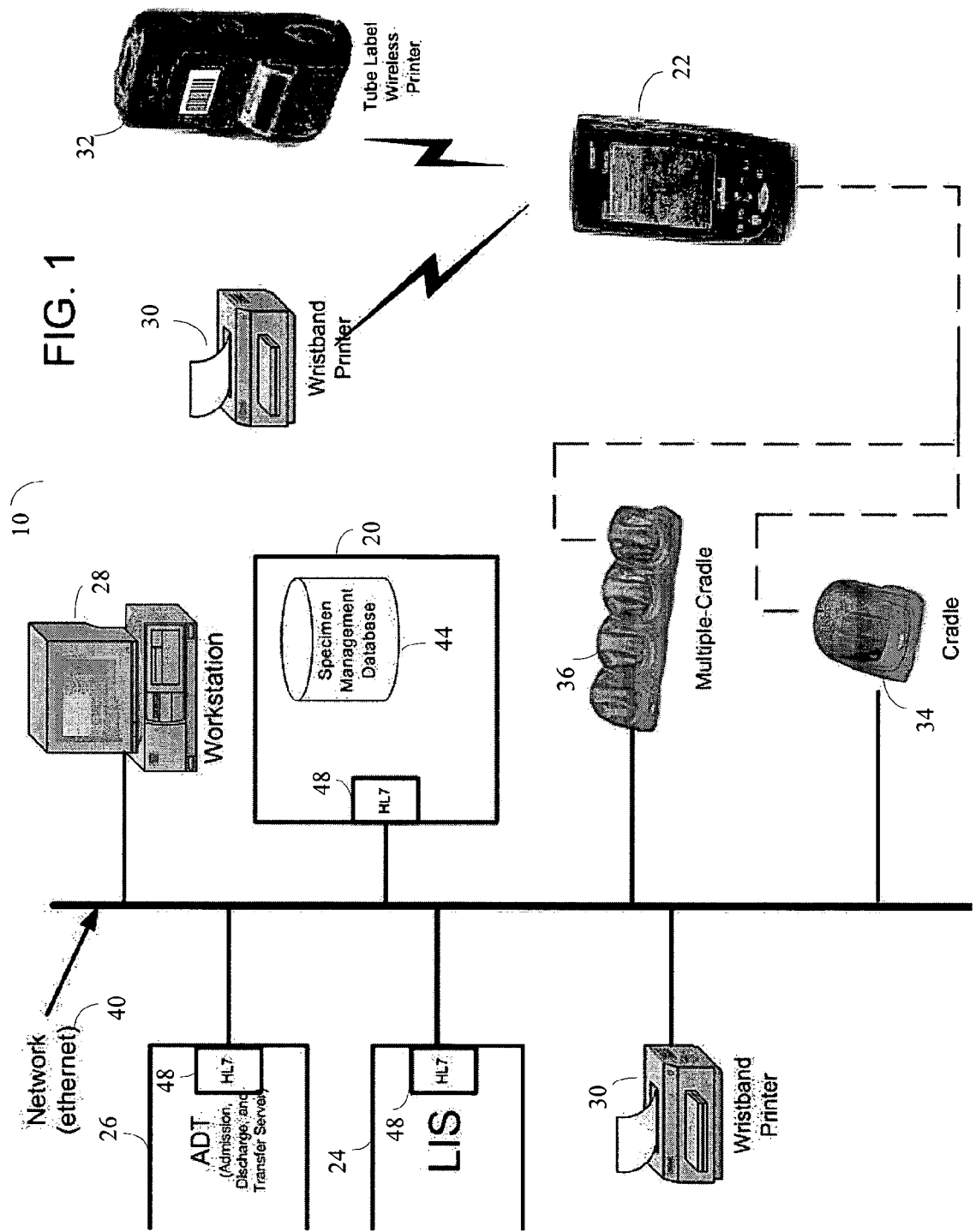

In accordance with the present invention, a patient information system 10 (FIG. 1) that includes a portable medical handheld device 22 and wireless printer 32 is provided. The device 22 uses handheld scanners for specimen collection procedures, similar to those commonly done in hospitals. In addition, the device 32 uses a portable printer with wireless capability for printing specimen collection container labels that include patient information and barcodes at the location of patient collection. For illustrative purposes, the system 10, including devices 22 and 32, will be described herein with reference to specimen collection procedures. It is to be understood that the system 10, including the devices 22 and 32, can also be used for monitoring and labeling in other similar applications (e.g. administration of therapeutics to patients). The system 10 can be the BD.id System available from Becton Dickinson and Company, Franklin Lakes, N.J.

In a preferred embodiment, the handheld device 22 allows a user such as a nurse or phlebotomist to match the specimen collection orders stored in the handheld 22 with the information scanned from the patient wristband, and to confirm that the specimen collection container 56 (FIG. 13) is the correct one for the tests ordered. A new bar code label 52 for the specimen container is printed on a printer with wireless capability (i.e. printing can be accomplished by means of a wired connection with the handheld or by wireless means between the printer and the handheld) at the patient's location. The new bar code label 52 includes the time and date of patient specimen collection and the user's name. The label 52 can be placed on the collection container 56, the patient's chart, or both. Additionally, the information about the time and date a container is collected can be electronically transmitted to a data storage element (e.g., the LIS 24 or SMS 44) for retrieval at a later time. In addition to transmission of the time and date a container is collected, the system may also collect and send the user's name who performed the collection, the draw method used to collect the specimen and, when applicable, a cancel status and a cancellation reason. Lastly, when replaced in its cradle 34, the handheld 22 synchronizes with the SMS 44, which is then able to communicate with the LIS 24.

With reference to FIGS. 1 through 4, the system 10 preferably comprises a server 20, a plurality of handheld devices 22 with data accessibility to the server 20, a plurality of printers with wireless capability 32 that have individualized barcodes and the capability to be portable, a LIS (Laboratory Information System) 24, and an ADT (Admission, Discharge, and Transfer) system 26. The system components are connected to a network 40 to allow for specific communication events to occur. Other embodiments may include aspects of the server 20 embedded into the LIS 24.

The term "handheld device" describes portable computers useful for executing specimen or medication management at the point of use. In a preferred embodiment of the present invention, the handheld has IR and barcode scanning capabilities and comprises a graphical user interface (GUI) for displaying information useful for collecting specimen samples from a patient. An example of such a portable handheld element is the Symbol Technologies PPT 8800 Series device.

Preferably, the handheld 22 includes a microprocessor, reading element such as a barcode scanner, and printing element. The microprocessor is capable of processing data relating to the identification information. The reading element ideally comprises a miniature identification code reader. The identification code reader could be a barcode scanner, imager, infrared identification reader, RFID reader or similar technology. A barcode scanner could be integrated into the medical handheld device or attached to the medical handheld device via an accessory device. Likewise, an RFID reader could be integrated into the medical handheld device so that when in the proximity of the container the container's RFID could be read by the reader.

The handheld 22 preferably includes a battery, a display screen for the GUI, depressible keys, communication circuitry, a memory element, a housing for securing all the handheld subcomponents, and a microprocessor. The handheld device could be a portable digital assistant (PDA), tablet PC, or notebook computer that includes a module and/or software for communicating with a server.

The handheld device 22 can download files and data for manipulation, run applications, or request application-based services from a file server. The handheld 22 can communicate with hospital computer systems (e.g., the LIS 24, ADT 26 and HIS 38) via the server 20. Alternatively, the LIS 24, for example, can be configured to communicate directly with the handheld 22. The handheld devices 22 can scan the barcode of a printer 32 with wireless capability in order to establish communication that allows for wireless printing of labels.

The printer 32 with wireless capability is intended for printing labels at the point of use, such as the location of sample collection. More specifically, in several locations within the healthcare setting, printers are needed for printing labels with patient information for downstream tracking and processing of the sample. An important part of the specimen collection label is the barcode, which can generally be described as the collection identification number. Ideally blood collection containers 56 (FIG. 13) would be available to the health care worker including a barcode 52 or RFID (radio frequency identification) tag communicating tube specific information to be registered with the portable handheld device 22 of the present invention. In one embodiment, the barcode label 52 is printed upon scanning of a collection container's barcode after the user and patient have both been scanned into the system. The barcode printer 32 can be located or housed on a phlebotomy cart or tray, or mounted in a patient's room. The printer 32 creates a customized label 52 containing the bar code accession number that the LIS 24 has assigned to the specimen. The printer 32 is preferably a portable printer such as a battery-powered thermal printer.

The Hospital Information System (HIS) 38 (FIG. 2) is a system developed with the objective of managing and streamlining the treatment flow of a patient in the hospital, along with all data associated with the patient necessary for efficient and organized healthcare service. Treatment flow includes, but is not limited to, specimen management, medication management, and transfusion management. The HIS 38 allows doctors and other staff to perform to their peak ability in an optimized and efficient manner. Most HIS 38 units are modular, thus ensuring sustained benefits through changes in technology such as integration with new and improved LIS 24 and ADT 26 systems.

An HIS 38 uses a network of computers to gather, process, and retrieve patient care and administrative information for most hospital activities to satisfy the functional requirement of the users. An HIS also helps to provide a decision support system for hospital authorities who develop and manage comprehensive health care policies.

An HIS 38 incorporates integrated computerized clinical information systems for improved hospital administration and patient health care. An HIS 38 also provides for accurate, electronically stored medical records for a single or multiple patients. Typically, an HIS 38 is a centralized information system designed for quick delivery of operational and administrative information and includes software capable of optimizing core data and other application modules customizable to the hospital or healthcare facility.

The term LIS 24 preferably defines a computer network comprised of industry standard network hardware and software (network and communication protocols) that functions to allow communication between the patient health record repository, the end user client applications running on various device types, and the various types of servers. This network can take the form of a cable-based or fiber optic network, a local area network (LAN), a wide area network (WAN), a virtual private network (VPN), the Internet, or any other type of network that allows communication between computing devices.

The LIS 24 is typically limited to laboratory information systems that organize and track information relating to laboratory tasks such as how orders are generated and communicated to the lab, how patients or samples are delivered, how the samples are accessioned and prepared, how testing is actually accomplished, and how results are communicated to healthcare providers. An LIS can also organize, track, and determine how the health enterprise is reimbursed for the work done in the lab, and how reimbursement information is exchanged.

Figure 2:
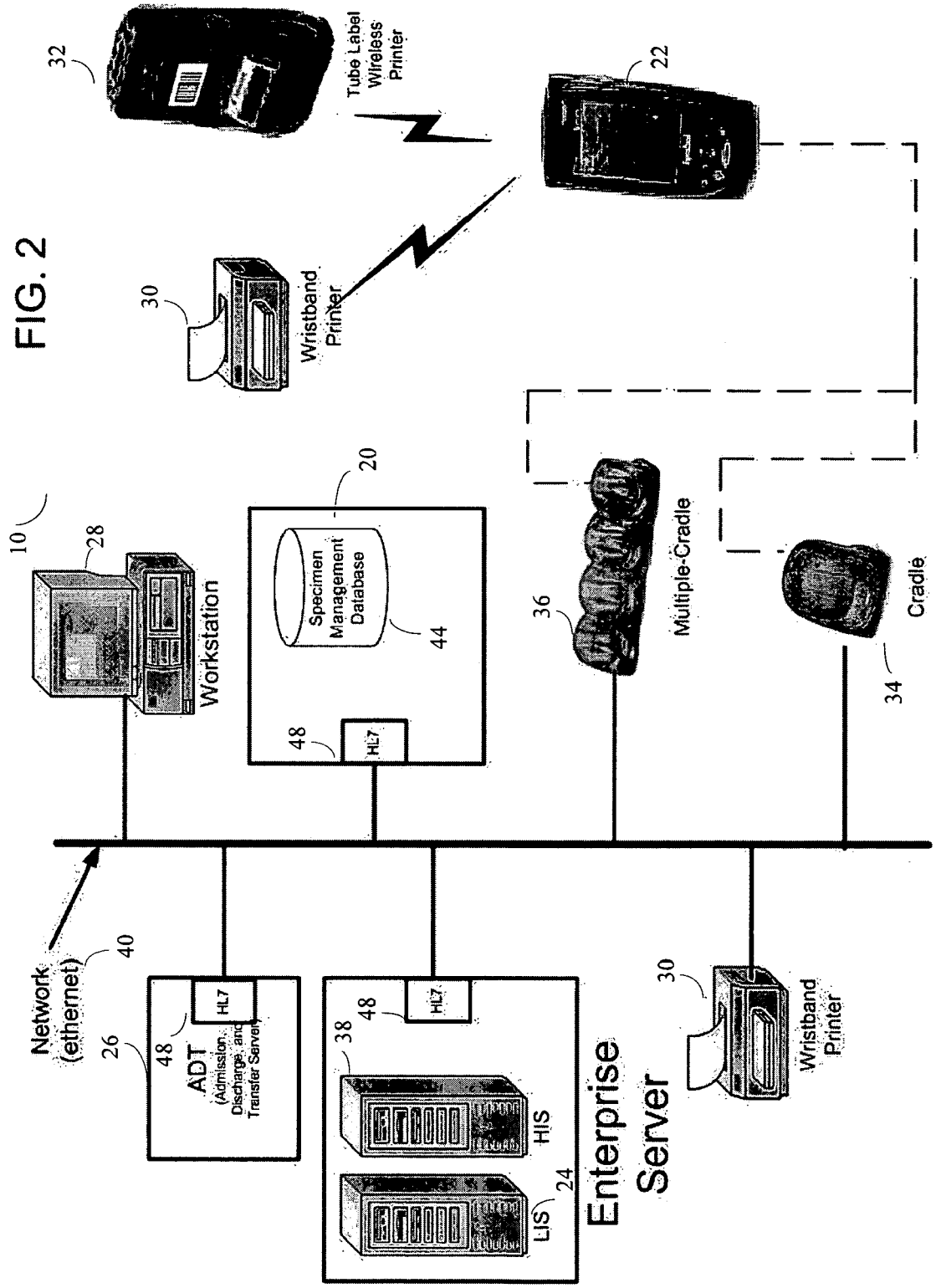
Figure 3:
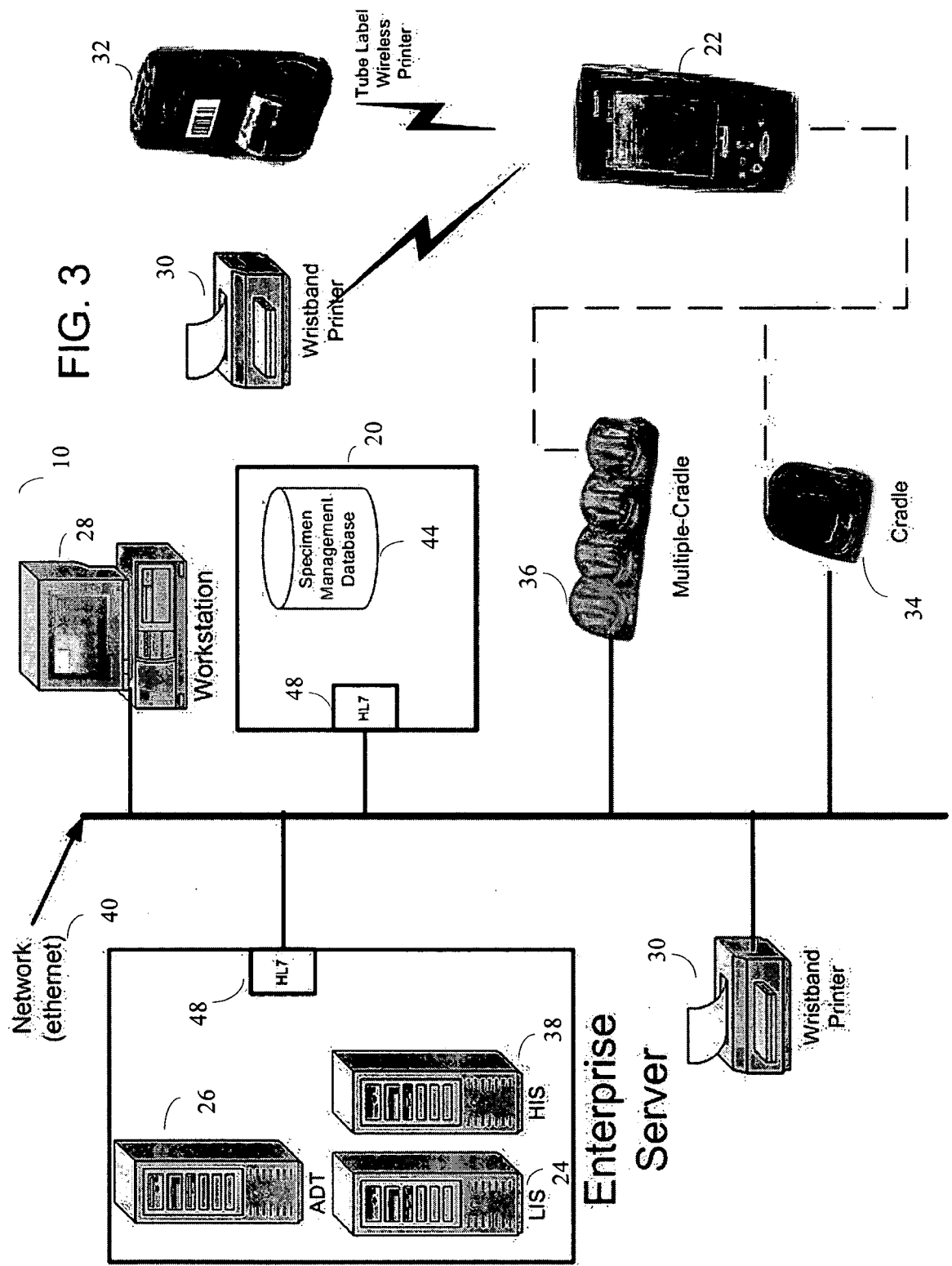

An enterprise server 42 can comprise the LIS 24 and the HIS 38, as shown in FIG. 2, or the ADT 26, LIS 24 and the HIS 38, as shown in FIG. 3. Alternatively, the HIS 38 and the ADT 26 operations can be combined into a single server as in FIG. 4, among other configurations.

In the system 10 of the present invention, the LIS 24 has a bi-directional interface with the server 10 to allow collection lists to be sent from the LIS 24 to the server 20, and to allow collection data and canceled orders to be sent from the server 10 to the LIS 24.

The LIS/HIS Data Interface 48 is an element for allowing communication among multiple modules that are sending and receiving data packets and signals across a network. Examples include Health Level Seven (i.e. HL7 3.0), ASTM 1238, ASTM 1394, Dbase, Comma Delimited ASCII, and Fixed Length.

The patient ID printer 30 with wireless capability is a printer typically designated for printing patient ID tags such as wristbands critical for accurate and efficient patient identification and safety. Patient ID tag printers are usually connected to a network and communicate with the ADT 26 and HIS 38 systems. Devices can also be provided to produce RFIDs along with the barcodes.

The server 20 may be a Specimen Management Server (SMS) 44. The SMS 44 is a server comprising a database and other programs and modules for running and integrating the LIS 24, HIS 38, and handheld 22 systems (e.g., a web server, a SQL server, a LIS to SQL parsing application, etc.). Typically, the SMS 20 creates and updates its database with information specific to patients and specimen samples collected from those patients. In certain embodiments, the SMS 20 is capable of executing a replication and synchronization service in order to maintain intermittent communication with the handheld 22. Functionality of the specimen management server 20 can be integral to the LIS 24, HIS 38, or both. In one embodiment of the present invention, the SMS 20 can be separate from the LIS 24 and HIS 38, but run on the same network as the LIS 24 in order to receive updated information related to sample orders and accession numbers generated by the LIS 24.

Orders for pending specimen collection are tracked in the LIS 24 and appear on the corresponding handheld device menu for processing. However, conditions in a health care setting frequently exist that require labels to be generated with temporary identification (i.e. a "Temp ID" label). One situation where a Temp ID label is needed arises when an order is not in the system and there is an immediate need to collect a specimen and connect the patient's identity to the collected specimen. For example, when a patient is moved from one location of a hospital to another location, a patient's order information might not be available on a handheld in the new location. Another situation requiring a Temp ID arises when a nurse has difficulty collecting specimens from a patient and wants to notify an additional user by generating a label to facilitate the collection process by the second user. For example, a Temp ID label can be generated when a nurse encounters a patient from whom it is difficult to collect a sample (e.g., due to a collapsed or difficult to find vein) and wants a more experienced phlebotomist to collect the sample.

Figure 5A:
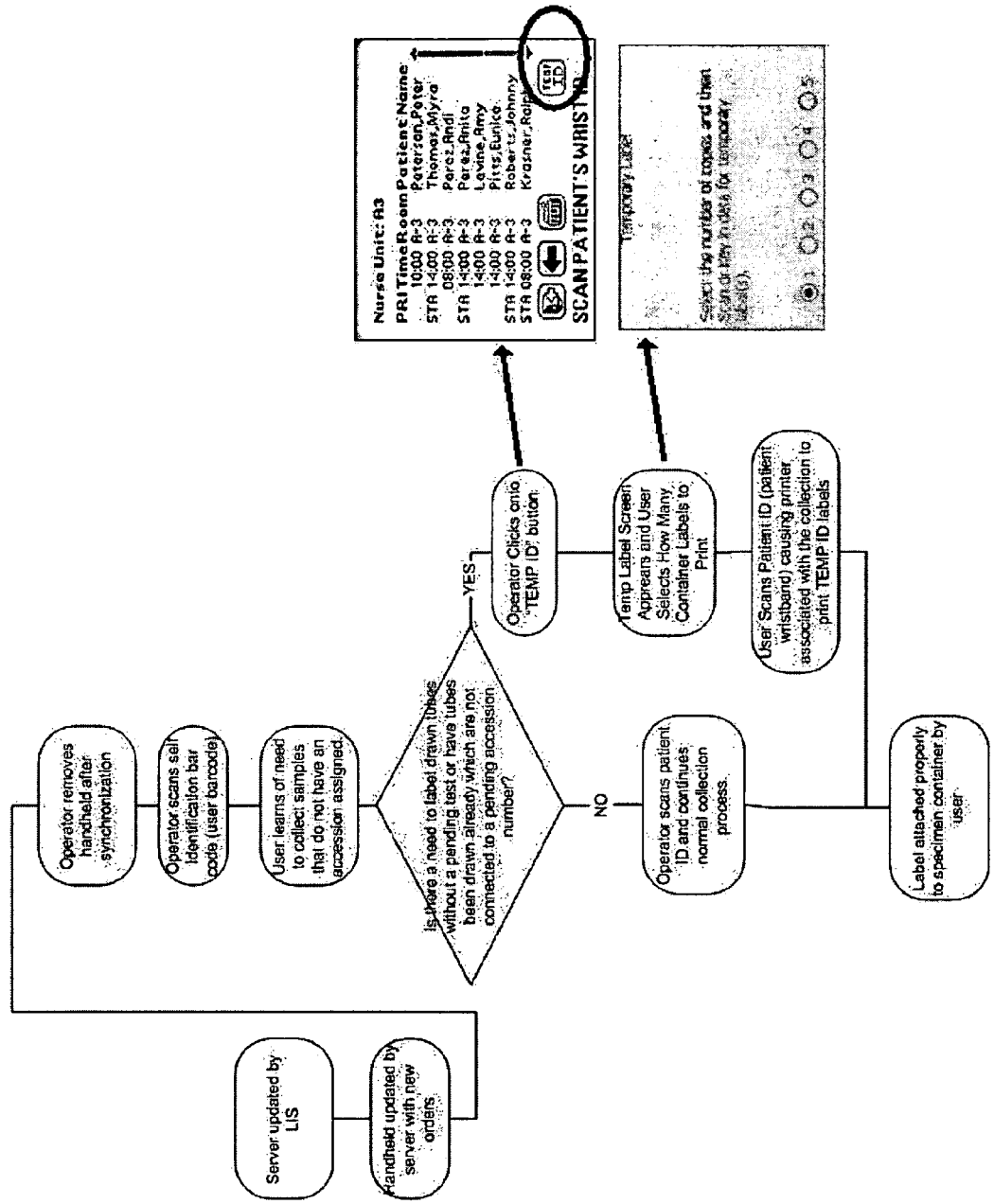

In two embodiments of the present invention, as shown in FIGS. 5A and 5B, the Temp ID is created by tapping a "Temp ID" radio button on the handheld device. A "Temp Label Screen" is then generated and displayed that allows the user to select how many copies of the Temp ID label to print. In one embodiment, the user then scans the Patient ID wristband (FIG. 5A) thereby causing the printer associated with the handheld to print the number of Temp ID labels requested for the scanned patient. In another embodiment, the user has the option either to scan the Patient ID wristband or to manually enter the patient ID number (FIG. 5B) into a Temp ID menu screen of the handheld device.

The following steps more fully explain the process of an embodiment of the present invention by which the handheld is used to generate a label for a sample that has not been ordered in the LIS 24 or does not appear in a location's handheld. A Temp ID label is placed on the patient specimen collection container 56 until the order has been entered into the LIS 24 or until the patient's location is updated in the patient information management system.

1. Log into the handheld device.
2. Select the location.
3. From the Patient List Screen, tap the Temp ID button.
4. A Temporary Label screen appears that allows the user to chose a radio button that identifies how many copies of the label are to be printed.
5. Scan the barcode on the patient's wristband or select the menu option on the handheld and enter the patient ID.
6. The handheld prints out the number of temporary patient ID labels requested.
7. Place the temporary ID label on the corresponding tube after collection of the sample.
8. Log out of the handheld and cradle it to receive new orders.
9. After the patient's order has been received by the patient information management system and downloaded to the handheld, log into the handheld.
10. Select the location.
11. At the Patient List Screen, scan the temporary ID label instead of scanning the patient's wristband.
12. The order list appears.
13. Tap on the order that corresponds to the tube with the temporary label (e.g. scan the red top tube temporary label for the test that requires a red top tube).
14. Tap the Manual Collect button to generate a specimen label for that tube.
15. Place the specimen label over the temporary ID label.
16. Repeat the process if additional specimen labels are needed.
17. Complete the workload screen.
18. Log out of the handheld and re-cradle the handheld.

Figure 6:
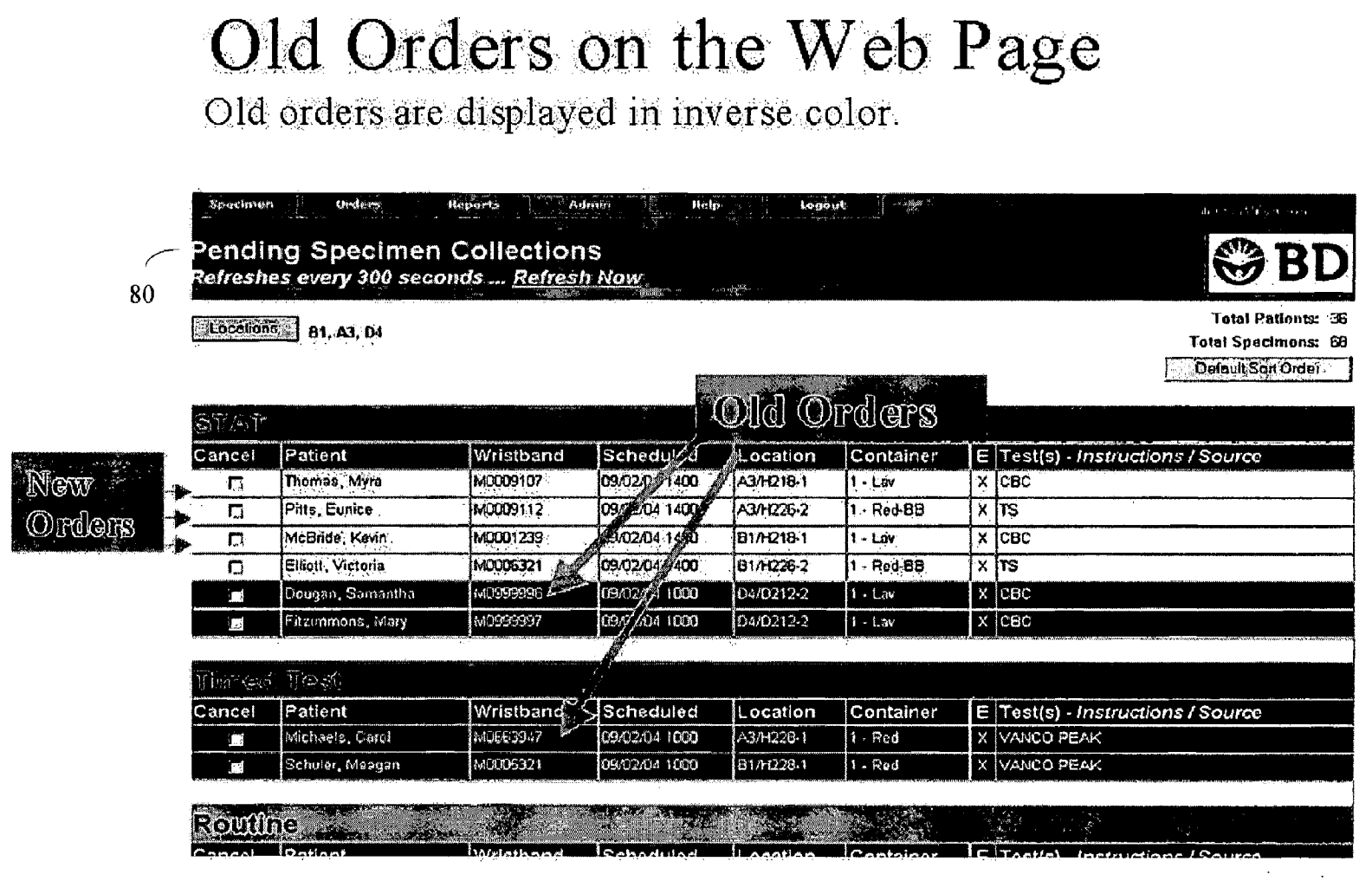

Frequently, specimen collections are required to be performed in a certain time window in order to ensure effective and expedient recovery or to provide periodic monitoring of patients. Typically, collection periods are tracked manually or on a central health care information system. Users of the patient information system are notified when a patient has past due orders by displaying old orders in inverse color on the Pending Specimens Collection web page (FIG. 6) of the patient information management system. To display in inverse colors means, for example, that if the background is white and the text is black, then when the order becomes old, the table cell background for that order will be black and the cell text will be white. A "past due" order is an order with a scheduled date and time that is older than the current date and time allowed by a user defined number of minutes. The responsible health care worker should check for past due orders at least once per shift and then collect, cancel or remove the orders from the patient information management system to prevent an inappropriate re-draw of patient specimens.

The present invention provides means for the handheld to identify and highlight old past due orders. In the preferred embodiment of the present invention, a patient information management system parameter named "Time Window (min) to show Past Due Orders Normally" may be set by the administrator or a designated user from 0-960 minutes, with the default set at 240 minutes. When the time to complete the order exceeds the number of minutes defined, the order will be displayed in a color other than the default color of text or will be displayed in reverse highlighting on the Patient List screen of the handheld device. In one embodiment of the present invention, past due orders will be highlighted in blue on the Patient List Screen 100 (FIG. 7). In addition, when a patient with past due orders is identified for specimen collection by the user, the handheld will display a "Past Due Order Warning" 104 to alert the handheld user.

In one embodiment of the present invention, the highlighting color is not configurable and the highlighting of past due orders cannot be disabled. However, the invention may be designed to allow the user of the handheld device to change the highlighting color or reverse highlight past due orders. In addition, the invention may be designed to disable highlighting.

In one embodiment of the present invention, a handheld configuration parameter named "Display old order warning dialog" may be set to determine if a Past Due Order Warning 104 will display on the handheld when a patient with past due orders is identified for specimen collection. The Past Due Order Warning 104 contains patient information and informs the user that the highlighted orders are past due and should be collected or removed from the system. The past due orders will continue to display in a highlighted state until the order has been properly dispositioned in the patient information management system.

For certain orders, tests that are time sensitive are required. In one situation requiring a timed test, samples must be analyzed within a certain time period from collection. In another situation, samples must be taken at a specified time interval. Timed tests are typically tracked manually or on a central health care information system in a hospital environment. The invention provides means for the handheld to display an alert to notify the user that a timed test is due for a particular patient. The timed test indicator may be configured to activate at a preset time before the timed test is due. The preset time may be configurable by the user. The user may be alerted through a visual display or audibly on either the handheld or the web page. The alert may be set to continue until the test has completed or for a set period of time after the timed test period has elapsed.

In one embodiment of the present invention, a flashing "clock" icon 112 (FIG. 8) is displayed on the handheld screen to indicate that there are patients with Timed Test(s) ordered. The icon will be present and flashing even if the handheld device is in the cradle, except when it is actively performing a sync operation. The icon will appear on the Location screen when the handheld is in the cradle before the user logs in. The Timed Test icon on the handheld is capable of being selected by the user. If the icon is selected prior to user log in, the handheld displays the facility (if applicable), location, time, room and bed for patients with pending Timed Test orders, but does not display the patient's name (FIG. 8, screen 106). Once the user is logged into the handheld, the icon appears on the Location screen and on the Patent List Screen. If selected from either screen, the handheld displays the facility, location, patient name, time, room and bed for pending Timed Test orders of patients within the time setting range of the Timed Test window (FIG. 8, screen 108).

In a preferred embodiment of the present invention, the information on the Timed Test screen is read-only so the user is not able to select one of the patients to display his or her orders. However, the invention may be designed with functionality to allow selection of one of the patients on the list to display his or her orders and to process orders for that chosen patient. The Timed Test icon is available for selection until one of the following occurs: (i) all pending Timed Test orders have been dispositioned, (ii) the current time falls outside the Timed Test window for the "Post Timed Test Alert Minutes" system parameter (i.e. the time is beyond the scheduled date and time for the Timed Test), or (iii) the Valid Data Timer has expired.

Figure 9:
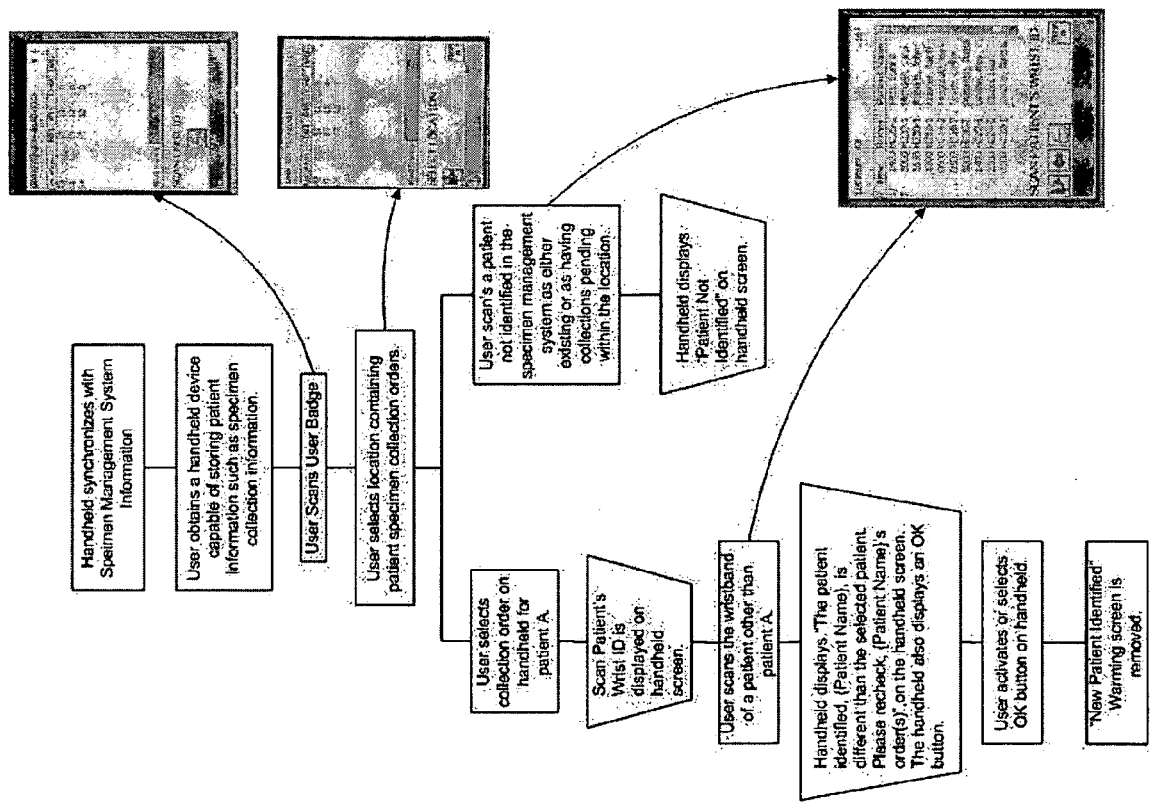
FIG. 9 depicts a logic diagram and several screen displays corresponding to the new patient identified warning of an embodiment of the present invention.

The invention provides means to display warnings when either a new patient wristband has been scanned after the user manually selects a collection order for another patient, or when a patient is scanned that does not exist in the system within the location. In one embodiment of the present invention, system logic is provided to generate warnings as per FIG. 9. In one case, a collection order for a patient has been selected by tapping on the patient's name on the Patient List screen 100, the handheld prompts the user to scan the chosen patient's wrist barcode identification. If the user scans a different patient's wristband, the user will be alerted with the following warning message on the handheld: "The patient identified {Name} is different from the selected patient. Please recheck {Name} order(s)." In another case, if the user scans the wristband of a patient that does not exist in the system or does not have any collections pending within the location, the following warning message is displayed on the handheld: "Patient Not Identified."

In order to ensure accurate tracking of patient information in order to avoid mistakes, a system is needed to notify health care personnel when samples have been received in the lab for processing. In a typical hospital and health care setting, the lab has an independent system (e.g. an LIS) for tracking samples received for processing that does not provide an automatic feedback mechanism to the health care information system. This method of tracking specimen collection samples can lead to errors that would require a patient specimen redraw from a single collection order. In addition, during periodic maintenance of any part of the health care information system, or if any part or all of the health care information system malfunctions for a period of time, a system or method is needed to ensure that the patient information system is only displaying specimens that have not been received in the lab.

Figure 10:
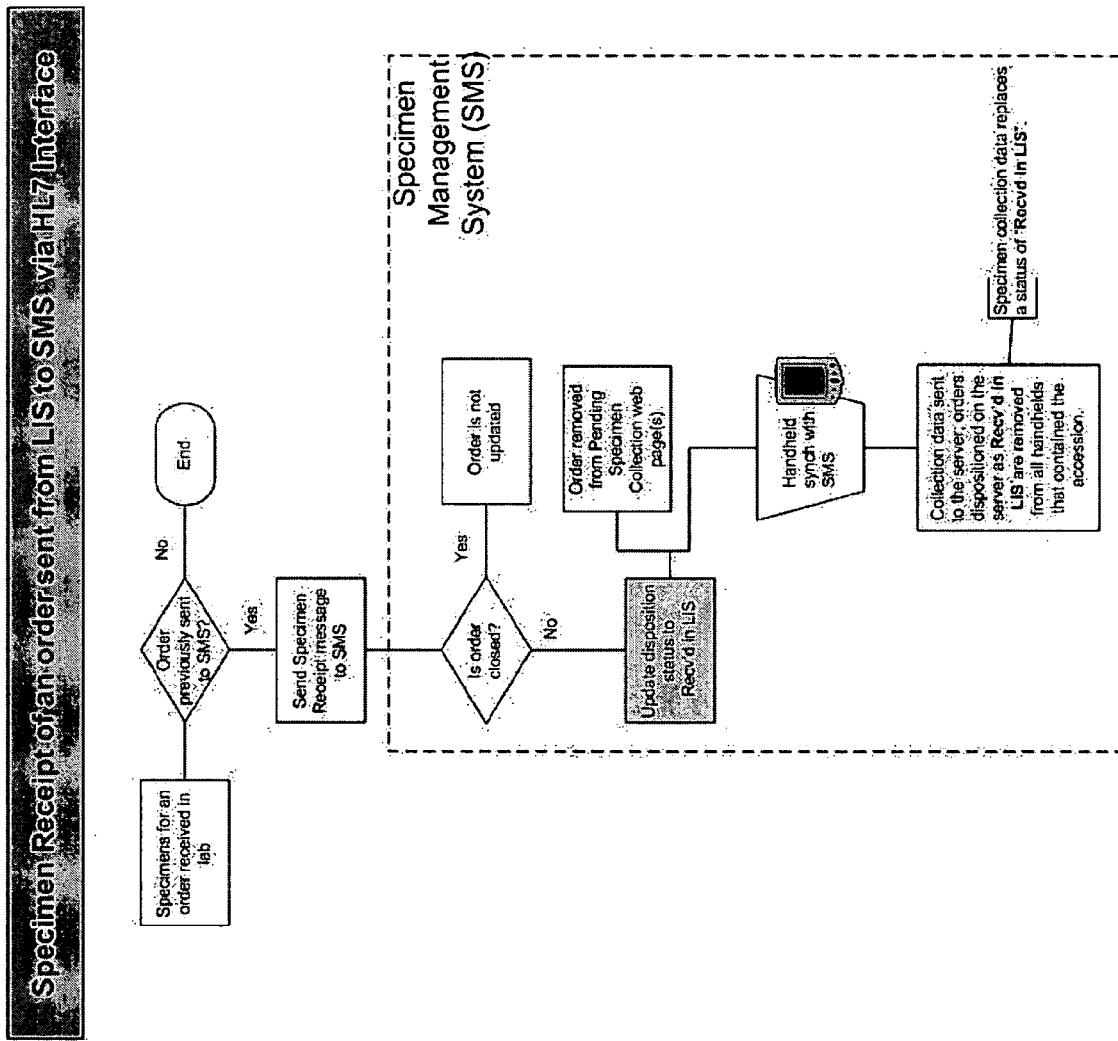
FIG. 10 is a logic diagram depicting a sequence of operations for specimen receipt processing by the LIS in an embodiment of the present invention.

The present invention has means to prevent multiple samples from being taken for the same specimen collection order (e.g. prevent patients from having their blood drawn multiple times for the same order) and to ensure system integrity by only displaying specimen collection orders that have not been completed and sent to the lab. In one embodiment of the invention, a message is sent by the LIS 24 to the SMS 20 of the present invention to indicate that a specimen has been received in the lab (FIG. 10). The SMS 20 includes capability to update an order's disposition status to "Received by lab" and to remove the order from the Pending Specimen Collections web page (FIG. 6, screen 80) of the patient information system once the order is confirmed by the LIS 24 as having been received by the lab. Orders collected inside the patient information system are removed as soon as the order is received and acknowledged in the lab or when the collecting handheld is docked, whichever comes first. Orders collected outside of the patient information system from locations defined to the patient information system are removed from the Pending Specimen Collections web page (FIG. 6, screen 80) at the workstation and handheld device. Orders collected outside of the patient information system from locations not defined in the system are removed from the Pending Specimen Collections web page (FIG. 6, screen 80) at the workstation.

If the patient information management system or its interface to the LIS 24 malfunctions or is taken down for maintenance while specimens are received in the lab, the present invention provides the capability to ensure data will not be lost. When the LIS 24 is down, the patient information management system can continue to be used for collection or cancellation of orders that are currently pending. As orders are dispositioned on the server, the system logs the data and holds the data in a queue until communication is re-established. When the LIS 24 is operational again, any data held in the patient information management system log for sending to the LIS 24 is then sent. Simultaneously, the LIS will re-initiate the sending of orders, cancellations and receipt messages to the patient information management system.

When the patient information management system is down, the LIS 24 cannot send order, cancellation and receipt messages to the system. If the system is down for an extended time, the LIS 24 will generate labels for pending orders and track the collection of specimens. When the patient information management system is again operational, the communication is re-established between the LIS 24 and the system. Collection order messages will then be sent to the system based on their schedule. In addition, any cancellations or receipt messages that occurred during the system downtime will be sent. These messages sent by the LIS 24 will disposition and reconcile the corresponding pending orders. Any orders that do not get reconciled may be manually removed from the patient information management system.

An Admission, Discharge, and Transfer server (ADT) 26 coordinates several aspects of patient processing in a hospital environment. In a standard hospital environment, a health care worker who needed to perform tasks, like updating a patient location, uses a workstation that is part of the ADT network. The present invention provides a means to allow the user to filter what ADT parameter updates are made in the patient information system (FIGS. 11 and 12).

The ADT 26 sends out several types of messages identified by a 3 character code. An "A08" message, for example, is considered a Demographic Update message. A message of this type can update any demographic for a patient (e.g. name, gender, date of birth, location, etc.).

In one embodiment of the present invention, the user can choose an ADT message type parameter on the Update an Existing Patient Configuration web page (FIG. 11). Another menu screen will then appear that allows the user to configure the patient information management system to allow a particular ADT message update (FIG. 12). System actions may be configured for the following set of parameters:

| ADT Parameter | Features |
| --- | --- |
| Add Patient | |
| Readmit | Option to update all fields |
| Update Name | |
| Update DOB/Gender | |

-continued

| ADT Parameter | Features |
| --- | --- |
| Update Patient Data | Option to enter extended data |
| Update Location | |
| Update Account | Option to update patient account/used on the patient identifier wristband |
| Update Extended Visit | Option to extend the auto-discharge date |
| Discharge Visit | |
| Discharge Patient | |
| Discharge Immediately | |

In order to ensure accurate patient information processing and specimen collection tracking, there is a need for providing a wireless connection between the handheld and a dedicated printer that is chosen by the user in order to avoid accidents and mistakes. The patient information management system includes a handheld device and a printer with wireless capability for printing labels at the patient's location.

In the health care environment, cabling may become damaged through handling. Furthermore, cabling may cause damage to equipment or collected specimens when health care workers perform required tasks (e.g. in the case of an emergency that requires sudden movement of hospital personnel). In the hospital setting, several printers with wireless capability could be present in the vicinity and within range of the wireless protocol employed by the handheld device. Therefore, the capability to dedicate a particular printer with wireless capability to the handheld is needed to avoid errors in labeling specimen collections and medical documents.

Figure 13:
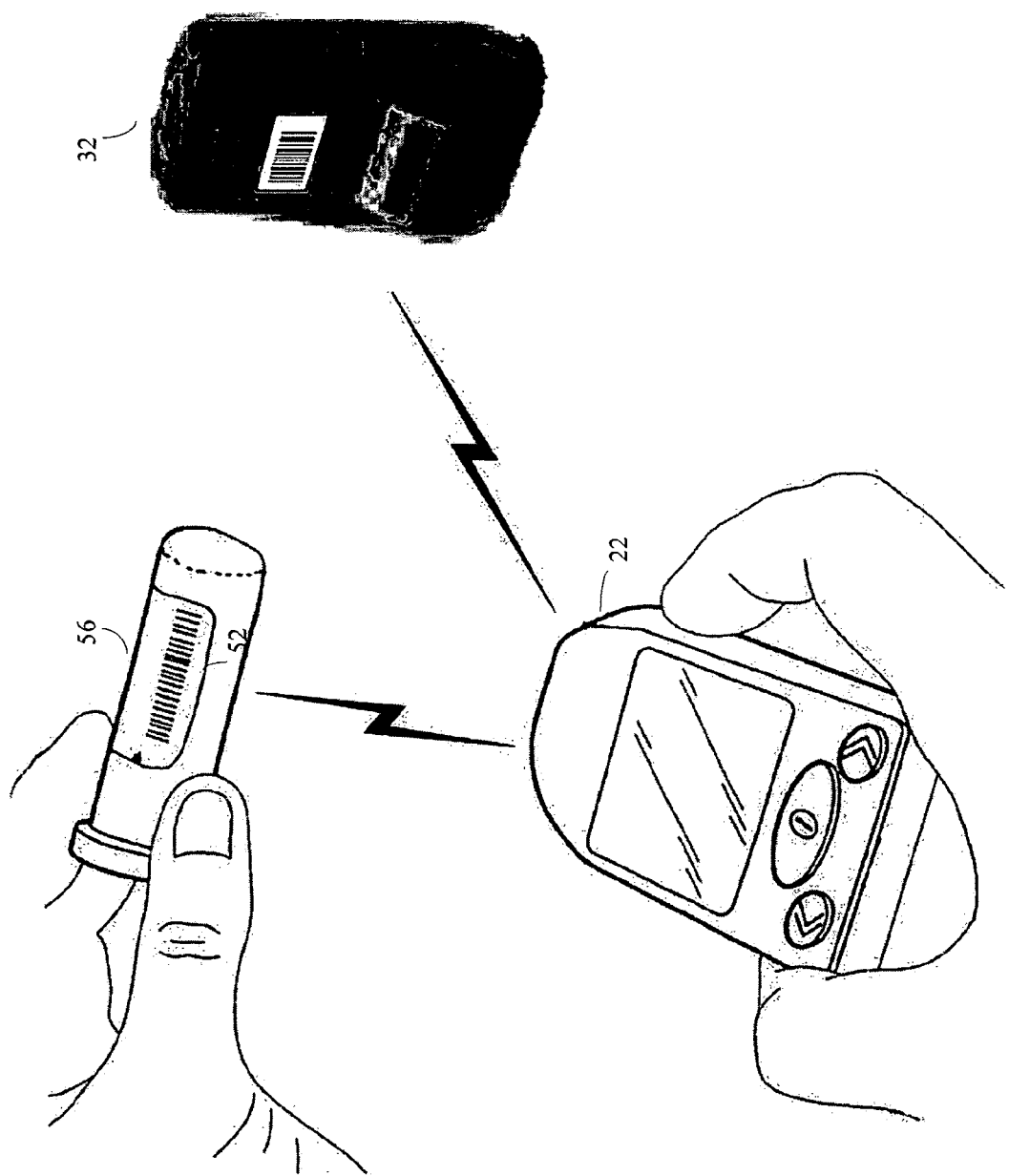
FIGS. 13 and 14 depict a diagram and flow chart, respectively, of a handheld device in use with a portable printer with wireless capability and a separate specimen tube with a corresponding bar code label attached in accordance with an embodiment of the present invention.

The present invention provides a means to dedicate a particular printer with wireless capability to a handheld device. In a preferred embodiment of the present invention, the discovery function of a standard wireless protocol (e.g. Bluetooth, 802.11b WiFi) is disabled in order to allow the handheld device to dedicate a printer by receiving printer identifier information. The handheld may receive printer identifier information from several means. In one embodiment, the handheld may receive printer identifier information by manually scanning an identification barcode attached to the printer (FIG. 13). In other embodiments, the handheld may receive printer identifier information from other sources such as an RFID tag or another system. The ability to deactivate the discovery function may be preset by the SMS system 20, LIS 24, HIS 38, system administrator may be given to one or more users of the patient information management system.

Figure 14:
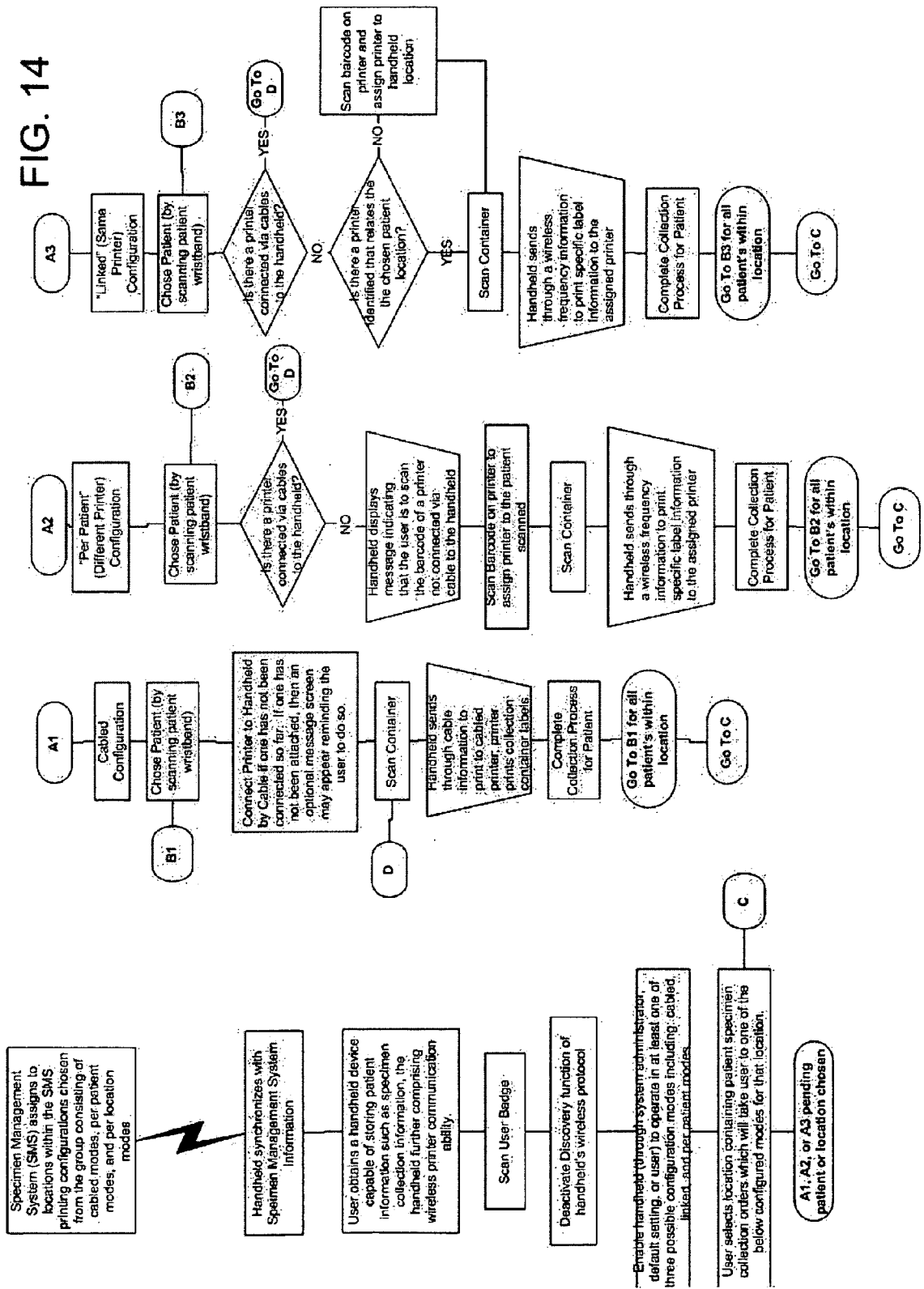

The handheld can communicate to the printer in one of the following three modes as shown for one of the embodiments of the present invention in FIG. 14:

1. Cabled: traditional method of connecting a physical cable between the printer and the handheld. Manually scanning the printer identification barcode is not required in cabled mode since a physical connection exists (FIG. 14, logic path A1).
2. Linked: a wireless print mode that requires the user to link the printer to the handheld by scanning the barcode on a printer only once for multiple patients (FIG. 14, logic path A3).
3. Per Patient: a wireless print mode that requires the user to link the printer to the handheld by scanning the barcode on a printer for each patient (FIG. 14, logic part A2).

A system administrator may initially set the default print mode as one of the three possible printer modes for each location such as a nursing unit or ward in a health care setting. In Linked Mode, the chosen printer remains in use for multiple patients. In an embodiment of the present invention, the chosen printer in Linked mode remains as the dedicated printer for the entire session in which specimen collections are taken from the same location. In Per Patient Mode, a new printer must be chosen after completing tasks for each patient. In an embodiment of the present invention, the printer chosen for a patient in Per Patient mode automatically deactivates (i.e. is no longer receptive to print messages from the handheld) after printing the required specimen collection labels for that patient.

In the Cabled mode, the health care worker will physically connect a printer via a cable to the handheld device to enable printing. In one embodiment of the present invention, functionality may exist to display a message screen on the handheld that will remind the user to connect a printer via a cable when the Cabled mode is set and a printer has not been attached (FIG. 14, logic path A1).

In the Linked mode, the health care worker will scan a chosen printer with wireless capability that may either be stationary or carried around on a cart when performing patient tasks. If the printer is carried around on a cart, the printer may be left in a stationary position on the cart or may be moved by the worker to a table or counter to ease processing of patient specimen collections or medical forms. The following steps comprise an overview of one embodiment of the present invention by which printing occurs in the Linked mode. Since the printer is "linked" to the handheld, the user only scans one printer one time.

1. Health care worker scans own User ID to log into the system.
2 Scan the wristband barcode on patient(1)'s wrist.
3 Scan the printer identification barcode attached to a printer.
4. Scan the specimen container barcode of the container(s) that will be used for specimen collection for patient(1).
5. Printing is activated until all labels are printed for patient(1).
6. Scan the wristband of patient(2).
7. Scan the specimen container barcode of the container(s) that will be used for specimen collection for patient(2)

In the Per Patient mode, the health care worker will scan a chosen printer with wireless capability that is mounted either inside or outside the patient's room. Typical applications where the Per Patient mode would be more advantageous include an intensive care unit and a respiratory care unit where an expedient method of printing in emergency situations is required. For example, if a nurse finds an intensive care patient in a state in which unordered samples are required and a portable printer malfunctions or is not readily available, a dedicated printer mounted in the room can be scanned for immediate generation of required labels. The following steps comprise an overview of one embodiment of the present invention by which printing occurs in the Per Patient mode. Since the printer mode is "per patient", the user must scan a printer for each patient being processed.

1. Health care worker scans own User ID to log into the system.
2 Scan the wristband barcode on patient(1)'s wrist.
3 Scan the printer identification barcode attached to a printer.
4. Scan the specimen container barcode of the container(s) that will be used for specimen collection for patient(1).
5. Printing is activated until all labels are printed for patient(1).
6. Scan the wristband of patient(2).
7. Scan the printer identification barcode attached to a printer.

8. Scan the specimen container barcode of the container(s) that will be used for specimen collection for patient(2).
9. Printing is activated until all labels are printed for patient(2).

In an embodiment of the present invention, if a printer is connected via a cable into the handheld device and either the Linked or Per Patient modes are configured and executed by choosing a particular location, the handheld sends the print message only to the cabled printer. In another embodiment of the present invention, if a printer is connected via a cable into the handheld device and either the Linked or Per Patient modes are configured and executed by choosing a particular location, the handheld sends the print message only to the Linked or Per Patient wireless printer. In another embodiment of the present invention, if a printer is connected via a cable into the handheld device and either the Linked or Per Patient modes are configured and executed by choosing a particular location, the handheld queries the user (e.g. through a menu option, icon, or message) for whether to send the print message to the cabled or wireless (Linked or Per Patient mode) printer.

In an embodiment of the present invention, printing mode options can be set for the entire hospital, by location, or for each patient session. In addition, wireless printing may be enabled globally for the hospital and a different default print mode for each location within the hospital may be assigned. Functionality may be provided on the handheld to allow a health care worker to change the default printing mode for a location. For example, a health care worker may need to override the default print mode in order to be able to use his or her own printer when the default printer malfunctions. The mode of dedicating a wireless printer may be configurable on the handheld in a menu option or may be enabled by simply scanning the barcode identifier of a new printer.

Several patient information system parameters must be configured to enable choice of wireless printing mode as follows:
1. Hospital Print Mode: determines whether wireless printing or cabled only printing is used throughout the hospital or health care setting.
2. Default Location Printing Mode: determines the default mode of printing used (i.e. Cabled Only, Linked or Per Patient) when the patient information system auto-learns a new location.
3. Locations: includes a field for Print Mode that determines the default mode of printing used (i.e. Cabled Only, Linked or Per Patient) for an existing location.

Although the present invention has been described with reference to several embodiments thereof, it will be understood that the invention is not limited to the details thereof. Various modifications and substitutions have been suggested in the foregoing description, and others will occur to those of ordinary skill in the art. All such substitutions are intended to be embraced within the scope of the invention.

What is claimed is:

1. A system for managing patient information comprising:
a printer for accepting data wirelessly for printing labels;
a scanner for reading patient identifier information, printer identifier information, and specimen container identifier information; and
a wireless handheld device for use with said scanner and with said printer for enabling said printer to be dedicated to said handheld device in order to perform printing of labels relating to at least one of patient information and specimen container information by scanning the printer identifier information of said printer and then using said printer identifier information to establish a wireless temporary local area network between said handheld device and said printer wherein said handheld device has the ability to cause said printer to perform label printing tasks wirelessly for a duration determined by selection of a print mode from a plurality of wireless print modes.

2. The system of claim 1, wherein said scanner is integrated into said handheld device.

3. The system of claim 1, wherein said handheld device provides instructions for printing of a temporary identification label.

4. The system of claim 3, wherein printing of said temporary identification label is caused in part by touching the display screen of said handheld device.

5. The system of claim 3, wherein a display screen is generated on said handheld device that allows a user to choose how many copies of said temporarily identification label to print.

6. The system of claim 1, wherein said handheld device is configured to generate a warning when patient information displayed on said handheld device does not match patient identification information received by the scanner.

7. The system of claim 1, wherein said handheld device is configured to display a message which confirms receipt of a specimen collection in a laboratory.

8. The system of claim 1, wherein said server is configured to update at least one patient information parameter with data from another system.

9. The system of claim 8, wherein the at least one patient information parameter is admission, discharge or transfer information.

10. The system of claim 1, wherein said printer is dedicated to said handheld device to perform label printing tasks wirelessly for at least one of several patients.

11. The system of claim 1, wherein said printer is dedicated to said handheld device to perform label printing tasks wirelessly during information processing for only a first patient, and then additional printer identification information is received by the scanner to perform label printing tasks wirelessly for only a second patient.

12. A system for managing patient information comprising:
a printer for accepting data wirelessly for printing labels;
a scanner for reading patient identifier information, printer identifier information, and specimen container identifier information; and
a wireless handheld device for use with said scanner and with said printer for enabling said printer to be dedicated to said handheld device in order to perform printing of labels relating to at least one of patient information and specimen container information by scanning the printer identifier information of said printer and then using said printer identifier information to establish a wireless temporary local area network between said handheld device and said printer wherein said handheld device has the ability to cause said printer to perform label printing tasks wirelessly,
wherein the handheld device is configured for enabling highlighting of past due requests for patient specimen collection.

13. The system of claim 12, wherein a highlighting color or highlighting method is configurable by a user.

14. A system for managing patient information comprising:
a printer for accepting data wirelessly for printing labels;
a scanner for reading patient identifier information, printer identifier information, and specimen container identifier information; and
a wireless handheld device for use with said scanner and with said printer for enabling said printer to be dedicated to said handheld device in order to perform printing of labels relating to at least one of patient information and specimen container information by scanning the printer identifier information of said printer and then using said printer identifier information to establish a wireless temporary local area network between said handheld device and said printer wherein said handheld device has the ability to cause said printer to perform label printing tasks wirelessly, wherein said handheld device permits display of an icon when a particular specimen collection order is time sensitive.

15. The system of claim 14, wherein said icon is displayed after a predetermined interval.

16. The system of claim 14, wherein the time sensitive nature of said specimen collection order is based on a periodic need for specimen collection.

17. The system of claim 14, wherein said time sensitive nature of said specimen collection order is based on a maximum allowable time interval between specimen collection and specimen testing.

18. A method of printing patient specimen collection labels by using a patient information management system, said method comprising the steps of:
receiving identification information for a first patient;
receiving identification information for a printer thereby dedicating said printer to print information received from said printer for said first patient for a duration determined by selection of a print mode from a plurality of wireless print modes;
receiving identification information for a specimen collection container for said first patient;
printing on said printer at least one label that includes patient information for said first patient;
receiving identification information for a second patient;
receiving identification information for a container for said second patient; and
printing on said printer at least one label that includes patient information for said second patient.

19. The method of claim 18, whereby said printer only prints information sent wirelessly.

20. A method of printing patient specimen collection labels by using a patient information management system, said method comprising the steps of:
receiving identification information for a first patient;
receiving identification information for a printer thereby dedicating said printer to print information received from said printer for said first patient for a duration determined by selection of one from a plurality of wireless print modes;
receiving identification information for a specimen collection container for said first patient;
printing on said printer at least one label that includes patient information for said first patient;
receiving identification information for a second patient;
receiving identification information for a container for said second patient; and
printing on said printer at least one label that includes patient information for said second patient,
whereby a display on said handheld device prompts a request to determine whether printing will occur on a printer connected by a cable or a printer chosen by scanning printer identifier information in order to establish a wireless temporary local area network.

21. A method of printing patient specimen collection labels by using a patient information management system, said method comprising the steps of:
receiving identifier information for a first patient;
receiving identification information for a printer thereby dedicating said printer to print information received from said printer for said first patient for a duration determined by selection of a print mode from a plurality of wireless print modes;
receiving identification information for a container to be used for specimen collection for said first patient;
printing at least one label for said first patient;
receiving identification information for a second patient;
receiving additional identification information for a printer thereby dedicating said printer to print information received from said printer for said second patient;
receiving identification information for a container to be used for specimen collection for said second patient; and
printing at least one label for said second patient.

22. The method of claim 21, whereby the printer only prints patient information sent wirelessly.

23. A method of printing patient specimen collection labels by using a patient information management system said method comprising the steps of:
receiving identifier information for a first patient;
receiving identification information for a printer thereby dedicating said printer to print information received from said printer for said first patient;
receiving identification information for a container to be used for specimen collection for said first patient;
printing at least one label for said first patient;
receiving identification information for a second patient;
receiving additional identification information for a printer thereby dedicating said printer to print information received from said printer for said second patient;
receiving identification information for a container to be used for specimen collection for said second patient; and
printing at least one label for said second patient,
whereby a display on said handheld device prompts a request to determine whether printing will occur on a printer connected by a cable or a printer chosen by scanning printer identifier information in order to establish a wireless temporary local area network.

24. A method of managing patient information using a handheld device and a printer with wireless capability, said method comprising the steps of:
receiving patient identification information for a first patient;
receiving printer identification information thereby dedicating said printer to print at least one label for said first patient for a duration determined by selection of a print mode from a plurality of wireless print modes;
receiving identification information for at least one container that will be used for collecting a specimen of said first patient;
printing at least one label for said first patient;
receiving patient identification information for a second patient;
receiving identification information for at least one container that will be used for collecting a specimen for said second patient; and
printing at least one label for said second patient.

25. The method of claim 24, whereby said receiving of printer identification information is performed before printing for each patient.

* * * * *

UNITED STATES PATENT AND TRADEMARK OFFICE
CERTIFICATE OF CORRECTION

PATENT NO.         : 7,278,579 B2
APPLICATION NO.    : 11/274690
DATED              : October 9, 2007
INVENTOR(S)        : Cathy A. Loffredo et al.

Page 1 of 1

It is certified that error appears in the above-identified patent and that said Letters Patent is hereby corrected as shown below:

On The Title Page

Item (75) Inventors:  delete "Macleau" and replace with --Maclean--

Signed and Sealed this

Eighteenth Day of December, 2007

JON W. DUDAS
*Director of the United States Patent and Trademark Office*